United States Patent [19]
Wolbring et al.

[11] Patent Number: 5,456,675
[45] Date of Patent: Oct. 10, 1995

[54] PORT CANNULA ARRANGEMENT FOR CONNECTION TO A PORT

[75] Inventors: Peter Wolbring, St. Wendel; Dirk Anderheiden, Usingen, both of Germany

[73] Assignee: Fresenius AG, Bad Homburg von der Hohe, Germany

[21] Appl. No.: 221,053

[22] Filed: Mar. 31, 1994

[30] Foreign Application Priority Data

Apr. 8, 1993 [DE] Germany ............. 43 11 715.5

[51] Int. Cl.⁶ ............................................. A61M 25/00
[52] U.S. Cl. .................. 604/280; 604/164; 604/167; 604/256
[58] Field of Search .................. 604/280, 283, 604/167, 256, 905, 86, 88, 164, 93

[56] References Cited

U.S. PATENT DOCUMENTS

| | | | |
|---|---|---|---|
| 5,062,836 | 11/1991 | Wendell | 604/167 |
| 5,114,408 | 5/1992 | Fleischhaker et al. | 604/256 X |
| 5,195,994 | 3/1993 | Dieringer | 604/905 X |
| 5,203,775 | 4/1993 | Frank et al. | 604/256 |
| 5,242,423 | 9/1993 | Goodsir et al. | 604/283 X |
| 5,273,546 | 12/1993 | McLaughlin et al. | 604/167 |

*Primary Examiner*—John D. Yasko
*Attorney, Agent, or Firm*—Jack Schuman

[57] ABSTRACT

Main cannula arrangement (10) with a metal cannula (12) and a connecting piece (14), featuring a valve (46), which is closed in the disconnected state and open in the connected state.

24 Claims, 1 Drawing Sheet

PORT CANNULA ARRANGEMENT FOR CONNECTION TO A PORT

The invention pertains to a port cannula arrangement for connection to a port. This arrangement features a port cannula made of metal, with a connecting piece on its proximal end. The connecting piece features a female Luer cone for receiving a tube system. The port cannula is surface-ground on its distal end. This port cannula arrangement also features a valve arrangement for opening and closing the access to the port cannula.

The port cannulas are used to provide access to an implanted port system. A port system of this type ordinarily serves to provide internal access for the application of liquid medicines and similar substances. These substances are supplied to a blood vessel via a catheter tube, which is connected to the port. A port system of this type thus represents the actual access to a vein. This port system displays a valve function by means of its closed septum and/or its capillary arrangement.

Typical port cannula systems feature a port cannula made of metal, which is provided with a connecting piece on its distal end. The connecting piece in turn is provided with an inner cone (ordinarily a female Luer cone). The inner canal of this connecting piece is thus connected to the cannula canal with respect to flow, without providing any type of closing element at this point. An infusion line system is ordinarily connected to this connecting piece by means of a male Luer connecting piece, through which the patient receives a supply of the medicines to be infused and similar substances. The applicant distributes a system under the name "INTRAPORT", in which a 3-way cock is provided in the infusion line, in order to make it possible to perform multiple injections when medicine is administered or when a blood sample is drawn via the implanted catheter system. In clinical practice, the puncture cannula is thus initially connected to the shutoff cock. A syringe filled with saline solution, for example, is then applied, and the injection system is deaerated. The port is punctured and flushed with the deaerated system, in order to determine whether the implanted catheter system is functional. The cock is subsequently closed, the syringe is removed, and another syringe—which contains the medicine to be administered—is applied. The cock is reopened, and the medicine is injected. The cock is subsequently closed again, and a syringe—which is usually filled with heparinized saline solution—is applied. The cock is opened, and a heparin block is set, in order to prevent the catheter system from becoming obstructed and unusable due to the formation of thrombi. Finally, the cannula is withdrawn from the port casing. During this withdrawal, it is necessary to maintain a slight positive pressure in the syringe while the cannula tip is still within the port casing.

The aspiration of blood involves essentially the same procedure.

The handling of this system in the injection of medicines or the aspiration of blood is very complicated. As a result, there is a great risk of handling errors.

However, catheter or cannula valves which prevent return flow have been known for a long time. For example, they have been used for years in the applicant's catheter system under the name "CAVATHETER". Valves of this type are provided in the catheter connector and/or in the connector of the cannula made of PTFE. (The catheter is inserted through the capillary of this PTFE cannula.) In both cases, the function of these valves is to prevent a return flow of blood when the catheter is being inserted. They are also intended to counteract the risk of air embolisms. Catheter systems of this type have been introduced by German patents 28 17 102, 29 18 326, and 30 00 903, for example. Each of these describes a connecting piece for a cannula which is provided with a slotted valve disk. However, the above-mentioned handling problems are not eliminated by these connecting pieces, because these connecting pieces must be applied to the port cannula.

On the other hand, one-piece cannulas with non-return valves have also been suggested—in DE 41 37 019 C, for example. In this case, a valve is located directly within the cannula. For one thing, this is difficult to implement from a technical standpoint. Furthermore, it can only be applied to vein cannulas, in cases in which a certain vein thickness can be assumed. DE 42 04 002 A provides a device for drawing blood and performing injections; this device also involves a port cannula. The cannula introduced here is punched through a rubber membrane by means of an elastic spring. However, this rubber membrane can not be used with a port cannula. The reason is that every penetration of the membrane punches out particles which can either clog the port catheter or be flushed into the patient. For this reason, special port cannulas (for example, the so-called Huber needle) are used to penetrate the port. An attempt is made to punch the port as seldom as possible, in order to produce as few particles as possible. For this reason, the port cannula is supposed to be left untouched in various handling operations.

The invention is thus based upon the problem of providing a port cannula system of the type described at the beginning of this description. This port cannula system is intended to present the fewest possible handling problems for the treating physician and cause the least possible discomfort for the patient, as is caused by the continual movement of the inserted cannulas.

The solution of this problem is achieved by providing a port cannula for puncturing the septum of an internally located port with minimum material damage. The port cannula has a metal cannula which is surface ground at the distal end and which proceeds into a connecting piece at its proximal end. A valve, located within the connecting piece, closes off access to the metal cannula in a germproof manner. The design of the valve permits the valve to be opened when the connecting piece is entered by a section of a complementary connecting piece for the purpose of establishing a fluid connection to a syringe or similar device.

The cannula system invented here consists of two functional elements. The first functional element is the injection cannula itself, which can also be a special cannula—for example, for the puncturing of implanted port systems or catheter systems. The second functional element is the valve that is provided in the connecting piece of the cannula. This valve is opened by the male Luer cone of an applied syringe or a connected tube system. When the cone-shaped connecting system is removed, the valve automatically blocks the return flow of fluids. In this way, the return flow of this fluid is prevented after natural or artificially-created body cavities have been punctured.

The arrangement of the non-return valve provided by the invention makes it possible to dispense with the 3-way cock used in the INTRAPORT system. At the same time, this non-return valve immediately closes off the port cannula when a syringe or tube system is removed. This prevents the further creation of negative pressure, which would cause body fluid to be drawn back.

The arrangement of the non-return valve provided by the invention within the connecting piece is novel, insofar as it previously seemed impractical to combine a steel port cannula with the non-return valve commonly associated with a catheter. The reason was that only fluids are ordinarily supplied to the port, and the use of a three-way cock has seemed adequate.

It is especially practical to place this block directly at the point of connection between the port cannula and the system with which it is being connected. The reason is that the canals on both sides of the valve block can be safely filled with infusion fluid, so that the risk of air embolisms can be prevented with certainty. This is not assured in open systems, because the negative and positive pressures that occur frequently cause incomplete filling—especially within the port cannula. As a result, special preventive measures must be taken to remove the air which remains in the cannula.

When the valve provided by the invention is used in place of the conventional cock, it is possible to dispense with all of the handling required to operate the cock.

Aside from the injection of medicines into a port system or an implanted pump, other applications are also possible. These applications are characterized by one common element, namely, that they involve a puncture by means of a cannula, followed by multiple operations that absolutely require a change of external devices. It is thus possible to use the system provided by the invention to perform the percutaneous removal of urine from the bladder for diagnostic purposes, for example. It is also possible to use the system provided by the invention to draw large quantities of arterial blood for the purpose of blood gas analysis.

A sample embodiment of the invention is explained below, with references to the drawings.

Figure 1:
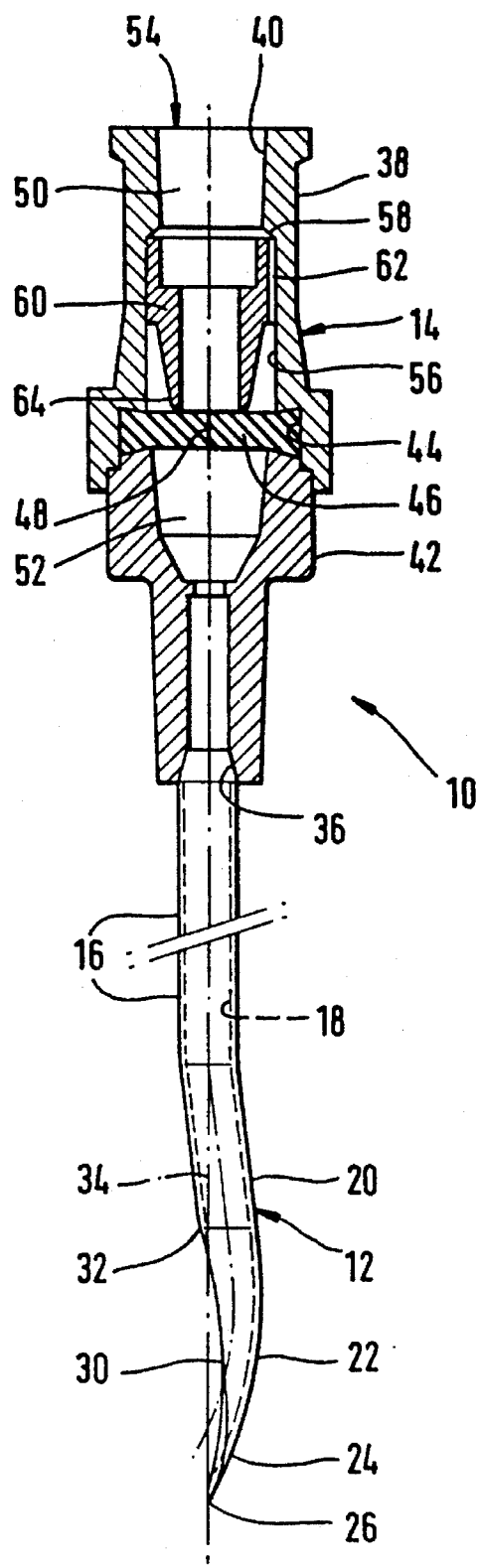
FIG. 1 shows a port cannula arrangement, in which the port cannula itself is represented in a side view, and the connecting piece is represented in cross section.
Figure 2:
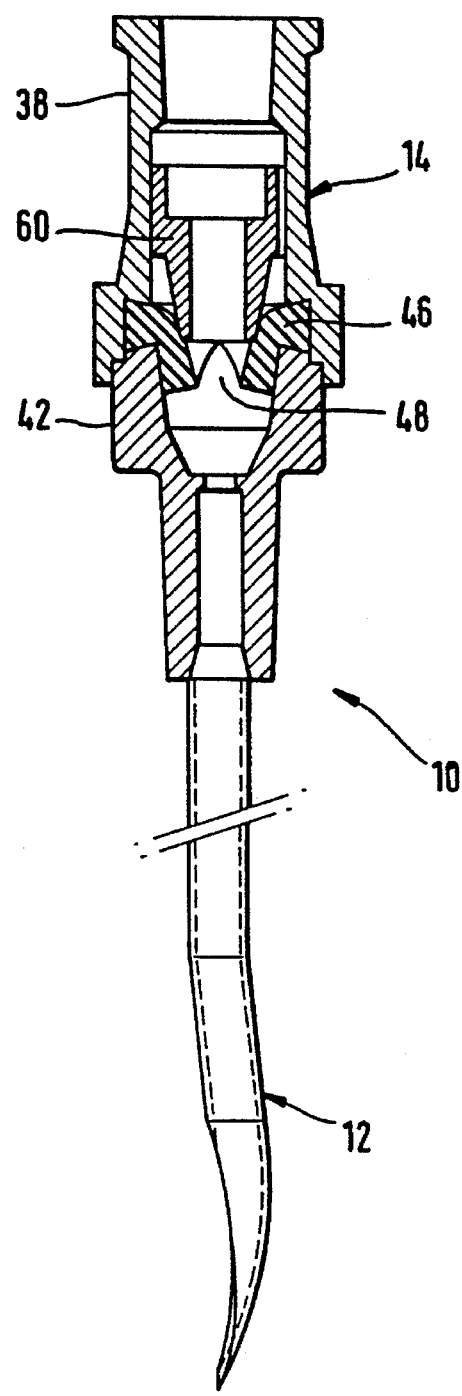
FIG. 2 shows the cannula arrangement with the membrane opened.

In FIGS. 1 and 2, the port cannula arrangement is identified by the number 10. This arrangement features a port cannula 12 and a connecting piece 14.

In an essentially straight segment 16, the port cannula 12 features a canal 18 represented by a dotted line. At its distal end, this segment 16 flows into a bent end segment 20. The canal 18 continues in a curved segment 22 and ultimately terminates in an insertion section 24 with a tip 26. A lumen opening 30 is provided in the insertion section. This lumen opening preferably displays a lenticular shape. However, it terminates in an opening tip in the region of the tip 26, while the end opposite the opening tip is rounded. Furthermore, the lumen opening 30 is located in the concave side of the curved segment 22. The lumen opening also features a rear edge 32 which is adjacent to the end segment 20 and built up inwardly into the curved segment 22. The tip 26 and the rear edge 32 lie on the imaginary central axis 34 of the canal 18.

The form of the port cannula 12 is not critical, but the cannula described in DE 41 01 231 A is preferred. For reasons of disclosure, reference is made to this cannula.

The proximal end 36 of the port cannula 12 flows into the connecting piece 14. This connecting piece 14 consists of an initial connecting section 38, which features an inner Luer cone 40, and, further forward, a second connecting section 42, which is connected to the proximal end 36 of the port cannula 12. Connecting sections 38 and 42 are connected to one another and welded. In the joined state, a groove 44 proceeding radially is formed in the region of the connection. A valve disk 46 in the form of circular disk of elastomeric material is held within this groove. This valve disk 46 is provided with a central slot 48, which terminates before the edge of the disk 46 on both sides.

The initial connecting section 38 and the second connecting section 42 feature central canals 50 and 52, respectively. When the slot 48 is open, these canals are connected to one another and to the canal 18 of the port cannula 12 with respect to flow.

According to the embodiment shown in FIG. 1, a cylindrical guide segment 56 is adjacent to the female inner cone 40. The diameter of this guide segment is greater than the smallest diameter of the inner cone 40, so that a step 58 is formed at the point of transition. This step 58 serves as a stop for a tubular element 60, which is held within the guide segment 56 in an axially displaceable manner. It is advantageous for the outer surface of this tubular element to be provided with longitudinal ribs 62 spaced at regular intervals across its circumference. The element 60 is supported against the cylindrical wall of the guide segment 56 by the longitudinal ribs 62. The conically tapered tip 64 of the element 60 contacts the valve disk 46.

In FIG. 2, the element 60 is represented in its advanced position, in which the slot 48 of the valve disk 46 is spread open. This advanced position is attained during the connection procedure, when the above-mentioned conical connecting piece of a tube system or syringe (not shown) pushes the element 60 forward.

When the tube system or syringe is disconnected, the restoring force of the valve disk 46 brings about the closure of the slot 48, thus causing the element 60 to be pushed back.

We claim:

1. Port cannula arrangement (10) for puncturing the septum of an internally located port with minimal material damage with a metal cannula (12) which is surface-ground at the distal end (20), and which proceeds into a connecting piece (14) at its proximal end (36), characterized as follows: a valve (46) which closes off access to the metal cannula (12) which is never exposed to blood under full vascular pressure in a germ proof manner is located within the connecting piece (14); the geometry of this valve is designed to allow the valve to be opened when the connecting piece is entered by a section of a complementary connecting piece for the purpose of establishing a connection to a syringe or similar device.

2. Port cannula arrangement as in claim 1, further characterized as follows: the valve is a valve disk (46) with a slot (48), which extends transversely across the connecting piece (14), said valve (46) being held in a ring-shaped groove (44).

3. Port cannula arrangement as in claim 1, further characterized as follows: a tubular operating element (60) is located between the insertion opening (54) and the valve disk (46); this operating element is guided in a longitudinally displaceable manner, such that in its retracted position, its end facing the valve disk (46) lies adjacent to the disk (46); in its advanced position, the operating element at least partially penetrates this disk for the purpose of opening the slot (48).

4. Port cannula arrangement as in claim 2, further characterized as follows: a tubular operating element (60) is located between the insertion opening (54) and the valve disk (46); this operating element is guided in a longitudinally displaceable manner, such that in its retracted position, its end facing the valve disk (46) lies adjacent to the disk (46); in its advanced position, the operating element at least partially penetrates this disk for the purpose of opening the slot (48).

5. Port cannula arrangement as in claim 2, further characterized in that the valve disk (46) is of elastomeric material.

6. Port cannula arrangement as in claim 3, further characterized in that the valve disk (46) is of elastomeric material.

7. Port cannula arrangement as in claim 4, further characterized in that the valve disk (46) is of elastomeric material.

8. Apparatus (10) for connection to a container having an extension providing a duct for introducing fluid from said container into a body or, selectively, for passing fluid from said body through said duct into said container, said apparatus comprising:

(a) a cannula (12) having a first end (24) and a second end (36), (b) an opening (30) in the first end (24) of said cannula (12) to be placed in communication with the interior of said body, (c) a connecting piece (14) having a first end (42) and a second end (38), the first end (42) of said connecting piece (14) being secured to the second end (36) of said cannula (12), (d) a hollow portion within said connecting piece (14), said hollow portion having a first chamber (50) and a second chamber (52), (e) said second chamber (52) communicating with the interior (18) of said cannula (12), (f) a resilient valve disc (46) mounted within said hollow portion of said connecting piece (14) between said first chamber (50) and said second chamber (52), said resilient valve disc (46) having a first face facing said first chamber (50) and a second face opposite said first face and facing said second chamber (52), (g) a slot (48) formed in said resilient valve disc (46) and extending from said first face to said second face thereof, said slot (48) being closed when said apparatus (10) is disconnected from said container thereby to seal said second chamber (52) from said first chamber (50), (h) a tubular element (60) slidably mounted within said first chamber (50) for movement toward and away from the first face of said resilient valve disc (46), said tubular element (60) having a first end (64) and a second end opposite said first end (64), (i) a central opening (54) extending through the second end (38) of said connecting piece (14) and providing access to the second end of said tubular element (60) and through said tubular element (60) to the first face of said resilient valve disc (46), (j) said cannula (12) and said second chamber (52) never being exposed to blood under full vascular pressure, (k) whereby, upon connecting said apparatus (10) to said container by inserting said extension of said container into said central opening (54), said extension will engage and depress the second end of said tubular element (60) and force the first end (64) thereof against the first face of said resilient valve disc (46) thereby to deform said resilient valve disc (46) and force open said slot (48), thus placing the first chamber (50) into communication with said second chamber (52) through said open slot (48) and permitting the passage of fluid between said first chamber (50) and said second chamber (52) through said open slot (48), (l) whereby, upon disconnection of said apparatus (10) from said container and removal of said extension from said central opening (54), said resilient valve disc (46) will revert to its undeformed state closing said slot (48) and preventing bacterial contamination from said first chamber (50) reaching said second chamber (52) and said body.

9. Apparatus as in claim 8, wherein:

(1) the external surface of said tubular element (60) is tapered inwardly adjacent the first end (64) thereof.

10. Apparatus as in claim 8, wherein:

(1) the central opening (54) extending through the second end (38) of said connecting piece (14) is the wide end of a female Luer cone.

11. Apparatus as in claim 8, wherein:

(1) said slot (48) extends along a diameter of said resilient valve disc (46) and stops short of both ends of said diameter.

12. Apparatus as in claim 8, wherein:

(1) the first end (64) of said tubular element (60) is adjacent the first face of said resilient valve disc (46) when said apparatus (10) is disconnected from said container.

13. Apparatus as in claim 8, wherein:

(1) said resilient valve disc (46) is made from elastomeric material.

14. Port cannula apparatus (10) for connection to a container having an extension providing a duct for introducing fluid from said container into a body through a port implanted in said body and having a sealing septum, said port cannula apparatus comprising:

(a) a cannula (12) having a first end (24) and a second end (36), said first end (24) being adapted to pierce said septum in said port thereby placing the interior (18) of said cannula (12) in communication with said port and the interior of said body, (b) a connecting piece (14) having a first end (42) and a second end (38), the first end (42) of said connecting piece (14) being secured to the second end (36) of said cannula (12), (c) a hollow portion within said connecting piece (14), said hollow portion having a first chamber (50) and a second chamber (52), (d) said second chamber (52) communicating with the interior (18) of said cannula (12), (e) a resilient valve disc (46) mounted within said hollow portion of said connecting piece (14) between said first chamber (50) and said second chamber (52), said resilient valve disc (46) having a first face facing said first chamber (50) and a second face opposite said first face and facing said second chamber (52), (f) a slot (48) formed in said resilient valve disc (46) and extending from said first face to said second face thereof, said slot (48) being closed when said port cannula apparatus (10) is disconnected from said container thereby to seal said second chamber (52) from said first chamber (50), (g) a tubular element (60) slidably mounted within said first chamber (50) for movement toward and away from the first face of said resilient valve disc (46), said tubular element (60) having a first end (64) and a second end opposite said first end (64), (h) a central opening (54) extending through the second end (38) of said connecting piece (14) and providing access to the second end of said tubular element (60) and through said tubular element to the first face of said resilient valve disc (46), (i) said cannula (12) and said second chamber (52) never being exposed to blood under full vascular pressure, (j) whereby, upon the first end (24) of said cannula (12)

piercing the septum of said port, the interior (18) of said cannula (12) is placed in communication with the interior of said port and the interior of said body, (k) whereby, upon connecting said port cannula apparatus (10) to said container by inserting said extension of said container into said central opening (54), said extension will depress the second end of said tubular element (60) and force the first end (24) thereof against the first face of said resilient valve disc (46) thereby to deform said resilient valve disc (46) and force open said slot (48), placing the first chamber (50) into communication with said second chamber (52) through said open slot (48) and permitting the passage of fluid from said first chamber (50) to said second chamber (52) through said open slot (48), (l) whereby, upon disconnection of said port cannula apparatus (10) from said container and removal of said extension from said central opening (54), said resilient valve disc (46) will revert to its undeformed state closing said slot (48), preventing bacterial contamination from said first chamber (50) reaching said second chamber (52), said port and said body.

15. Port cannula apparatus as in claim 14, wherein:
    (1) the external surface of said tubular element (60) is tapered inwardly adjacent the first end (64) thereof.

16. Port cannula apparatus as in claim 14, wherein:
    (1) the central opening (54) extending through the second end (38) of said connecting piece (14) is the wider end of a female Luer cone.

17. Port cannula apparatus as in claim 14, wherein:
    (1) said slot (48) extends along a diameter of said resilient valve disc (46) and stops short of both ends of said diameter.

18. Port cannula apparatus as in claim 14, wherein:
    (1) the first end (64) of said tubular element (60) is adjacent the first face of said resilient valve disc (46) when said port cannula apparatus (10) is disconnected from said container.

19. Port cannula apparatus as in claim 14, wherein:
    (1) said resilient valve disc (46) is elastomeric material.

20. Port cannula arrangement (10) for punctuating the septum of an internally located port with minimal material damage with a metal cannula (12) which is surface-ground at the distal end (20) and which extends into a connecting piece (14) at its proximal end (36), for the purpose of establishing a fluid connection to a syringe or similar device having a complementary connecting piece adapted to be inserted into the connecting piece (14), characterized as follows: a valve (46) which closes off access to the metal cannula (12) which is never exposed to blood under full vascular pressure in a germ proof manner is located within the connecting piece (14), the geometry of this valve (46) is designed to allow the valve to be opened by the complementary connecting piece on the syringe or similar device when the connecting piece (14) is entered by a section of said complementary connecting piece thereby establishing a fluid connection to said syringe or similar device.

21. Port cannula arrangement (10) for puncturing the septum of an internally located port with minimal material damage with a metal cannula (12) which is surface-ground at the distal end (20), and which proceeds into a connecting piece (14) at its proximal end (36), characterized as follows: a valve (46) which closes off access to the metal cannula (12) which is never exposed to physiological fluids under full pressure of said physiological fluids in a body in a germ proof manner is located within the connecting piece (14); the geometry of this valve is designed to allow the valve to be opened when the connecting piece is entered by a section of a complementary connecting piece for the purpose of establishing a connection to a syringe or similar device.

22. Apparatus (10) for connection to a container having an extension providing a duct for introducing fluid from said container into a body or, selectively, for passing fluid from said body through said duct into said container, said apparatus comprising:

(a) a cannula (12) having a first end (24) and a second end (36), (b) an opening (30) in the first end (24) of said cannula (12) to be placed in communication with the interior of said body, (c) a connecting piece (14) having a first end (42) and a second end (38), the first end (42) of said connecting piece (14) being secured to the second end (36) of said cannula (12), (d) a hollow portion within said connecting piece (14), said hollow portion having a first chamber (50) and a second chamber (52), (e) said second chamber (52) communicating with the interior (18) of said cannula (12), (f) a resilient valve disc (46) mounted within said hollow portion of said connecting piece (14) between said first chamber (50) and said second chamber (52), said resilient valve disc (46) having a first face facing said first chamber (50) and a second face opposite said first face and facing said second chamber (52), (g) a slot (48) formed in said resilient valve disc (46) and extending from said first face to said second face thereof, said slot (48) being closed when said apparatus (10) is disconnected from said container thereby to seal said second chamber (52) from said first chamber (50), (h) a tubular element (60) slidably mounted within said first chamber (50) for movement toward and away from the first face of said resilient valve disc (46), said tubular element (60) having a first end (64) and a second end opposite said first end (64), (i) a central opening (54) extending through the second end (38) of said connecting piece (14) and providing access to the second end of said tubular element (60) and through said tubular element (60) to the first face of said resilient valve disc (46), (j) said cannula (12) and said second chamber (52) never being exposed to physiological fluids under full pressure of said physiological fluids in said body, (k) whereby, upon connecting said apparatus (10) to said container by inserting said extension of said container into said central opening (54), said extension will engage and depress the second end of said tubular element (60) and force the first end (64) thereof against the first face of said resilient valve disc (46) thereby to deform said resilient valve disc (46) and force open said slot (48), thus placing the first chamber (50) into communication with said second chamber (52) through said open slot (48) and permitting the passage of fluid between said first chamber (50) and said second chamber (52) through said open slot (48), (l) whereby, upon disconnection of said apparatus (10) from said container and removal of said extension from said central opening (54), said resilient valve disc (46) will revert to its undeformed state closing said slot (48) and preventing bacterial contamination from said first chamber (50) reaching said second chamber (52) and said body.

23. Port cannula apparatus (10) for connection to a container having an extension providing a duct for introducing fluid from said container into a body through a port implanted in said body and having a sealing septum, said port cannula apparatus comprising:

(a) a cannula (12) having a first end (24) and a second end (36), said first end (24) being adapted to pierce said septum in said port thereby placing the interior (18) of said cannula (12) in communication with said port and the interior of said body, (b) a connecting piece (14) having a first end (42) and a second end (38), the first end (42) of said connecting piece (14) being secured to the second end (36) of said cannula (12), (c) a hollow portion within said connecting piece (14), said hollow portion having a first chamber (50) and a second chamber (52), (d) said second chamber (52) communicating with the interior (18) of said cannula (12), (e) a resilient valve disc (46) mounted within said hollow portion of said connecting piece (14) between said first chamber (50) and said second chamber (52), said resilient valve disc (46) having a first face facing said first chamber (50) and a second face opposite said first face and facing said second chamber (52), (f) a slot (48) formed in said resilient valve disc (46) and extending from said first face to said second face thereof, said slot (48) being closed when said port cannula apparatus (10) is disconnected from said container thereby to seal said second chamber (52) from said first chamber (50), (g) a tubular element (60) slidably mounted within said first chamber (50) for movement toward and away from the first face of said resilient valve disc (46), said tubular element (60) having a first end (64) and a second end opposite said first end (64), (h) a central opening (54) extending through the second end (38) of said connecting piece (14) and providing access to the second end of said tubular element (60) and through said tubular element to the first face of said resilient valve disc (46), (i) said cannula (12) and said second chamber (52) never being exposed to physiological fluids under full pressure of said physiological fluids in said body, (j) whereby, upon the first end (24) of said cannula (12) piercing the septum of said port, the interior (18) of said cannula (12) is placed in communication with the interior of said port and the interior of said body, (k) whereby, upon connecting said port cannula apparatus (10) to said container by inserting said extension of said container into said central opening (54), said extension will depress the second end of said tubular element (60) and force the first end (24) thereof against the first face of said resilient valve disc (46) thereby to deform said resilient valve disc (46) and force open said slot (48), placing the first chamber (50) into communication with said second chamber (52) through said open slot (48) and permitting the passage of fluid from said first chamber (50) to said second chamber (52) through said open slot (48), (l) whereby, upon disconnection of said port cannula apparatus (10) from said container and removal of said extension from said central opening (54), said resilient valve disc (46) will revert to its undeformed state closing said slot (48), preventing bacterial contamination from said first chamber (50) reaching said second chamber (52), said port and said body.

24. Port cannula arrangement (10) for punctuating the septum of an internally located port with minimal material damage with a metal cannula (12) which is surface-ground at the distal end (20) and which extends into a connecting piece (14) at its proximal end (36), for the purpose of establishing a fluid connection to a syringe or similar device having a complementary connecting piece adapted to be inserted into the connecting piece (14), characterized as follows: a valve (46) which closes off access to the metal cannula (12) which is never exposed to physiological fluids under full pressure of said physiological fluids in said body in a germ proof manner is located within the connecting piece (14), the geometry of this valve (46) is designed to allow the valve to be opened by the complementary connecting piece on the syringe or similar device when the connecting piece (14) is entered by a section of said complementary connecting piece thereby establishing a fluid connection to said syringe or similar device.

* * * * *